United States Patent [19]

Kenna

[11] Patent Number: 4,834,756
[45] Date of Patent: May 30, 1989

[54] BONE PROSTHESIS WITH POROUS COATING

[75] Inventor: Robert V. Kenna, Hackensack, N.J.

[73] Assignee: Pfizer Hospital Products Group, Inc., New York, N.Y.

[21] Appl. No.: 786,978

[22] Filed: Oct. 15, 1985

Related U.S. Application Data

[62] Division of Ser. No. 350,130, Feb. 18, 1982, Pat. No. 550,448.

[51] Int. Cl.$^4$ .............................................. A61F 2/28
[52] U.S. Cl. ...................................... 623/16; 623/66; 623/901
[58] Field of Search ....................... 623/16, 20, 22, 24; 428/547

[56] References Cited

U.S. PATENT DOCUMENTS

| | | | |
|---|---|---|---|
| 3,605,123 | 9/1971 | Hahn | 623/16 |
| 3,808,606 | 5/1974 | Tronzo | 623/16 |
| 3,843,975 | 10/1974 | Tronzo | 3/1 |
| 3,855,638 | 12/1974 | Pilliar | 3/1 |
| 4,017,911 | 4/1977 | Kafesjian et al. | 3/1.5 |
| 4,101,984 | 7/1978 | MacGregor | 3/1.5 |
| 4,206,516 | 6/1980 | Pilliar | 623/16 |
| 4,309,488 | 1/1982 | Heide et al. | 428/547 |
| 4,351,069 | 9/1982 | Ballintyn et al. | 3/1.912 |
| 4,374,669 | 2/1983 | MacGregor | 75/208 R |

OTHER PUBLICATIONS

Pilliar, R. M., "Bony Ingrowth into Porous Metal--Coated Implants", *Orthopaedic Review*, vol. IX, No. 5, pp. 85-91 (May 1980).

Bobyn et al., "The Optimum Pore Size for the Fixation of Porous-Surfaced Metal Implants by the Ingrowth of Bone". *Clin Orth & Rel. Res.*, No. 150, 1980 (pp. 263-270).

Nilles, J. L. et al., "Biomechanical Evaluation of Bone--Porous Material Interfaces", *J. Biomed. Mater. Res.*, vol. 7, pp. 231-251 (1973).

Hedley, A. K., "Present State, Problems, and Future Implications of Porous-Coated Implants", Chapter 16 in "The Hip Proceedings", C. V. Mosby Co., pp. 329-342 (1980).

Primary Examiner—Richard J. Apley
Assistant Examiner—David J. Isabella
Attorney, Agent, or Firm—Charles J. Knuth; Peter C. Richardson; Lawrence C. Akers

[57] ABSTRACT

An improved metallic bone prosthesis having a porous coating for bone ingrowth or interlocking with bone cement is disclosed. The porous coating comprises two layers of generally ball-shaped metallic particles bonded together at their points of contact, e.g. by sintering, and defining between them a plurality of connected interstitial pores having an average pore size of from about 350 microns to about 500 microns. A high resistance to failure at the coating-substrate and bone-coating (or cement-coating) interfaces is achieved with the use of the improved prosthesis. Also disclosed are a novel method for affixing the porous coating to a metal substrate, and a knee joint prosthesis having bearing portions designed so that the function of said prosthesis closely approximates that of the natural knee.

2 Claims, 1 Drawing Sheet

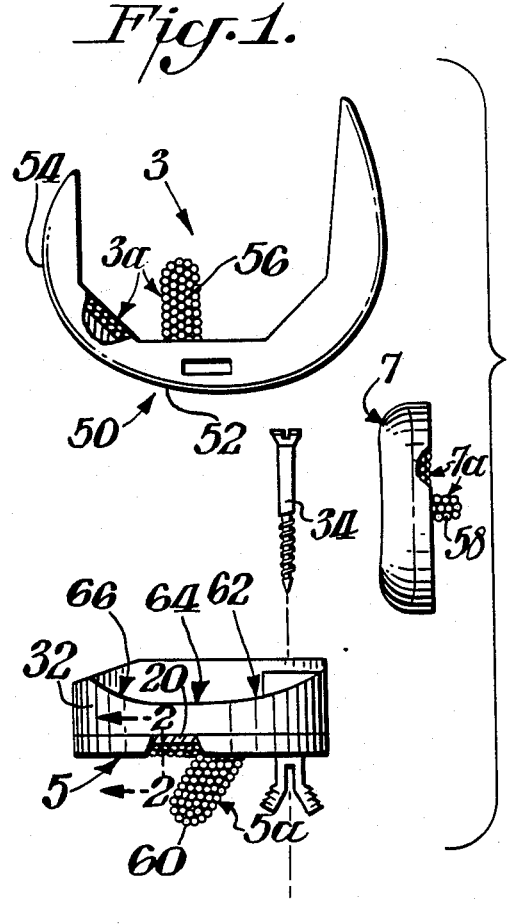
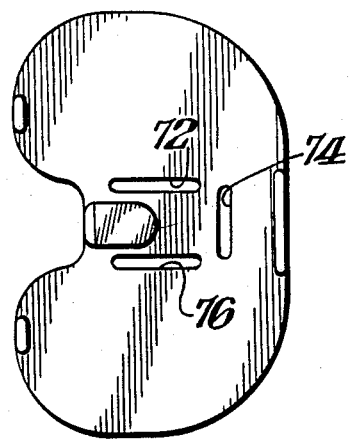
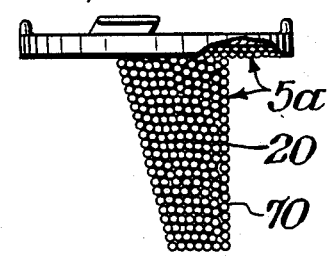
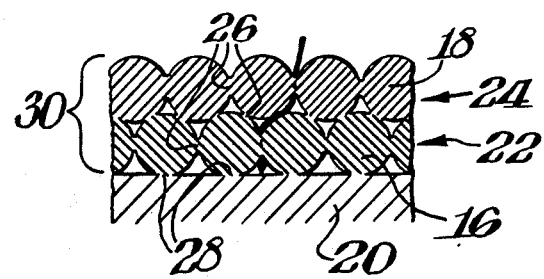

BONE PROSTHESIS WITH POROUS COATING

This is a division of application Ser. No. 350,130, filed on Feb. 18, 1982, now U.S. Pat. No. 4,550,448.

BACKGROUND OF THE INVENTION

It is well known in the medical arts to provide a metallic bone prosthesis with a porous metallic coating too enhance the fixation of the prosthesis to the patient's bone. Such fixation is generally achieved by either cementation or tissue ingrowth, or a combination of these techniques. The bone cement or freshly grown bone tissue occupies pore volume in the porous coating and thereby serves to lock the prosthesis in place. Fixation by tissue ingrowth has been recommended by many workers in the field of orthopedics as a means of eliminating or alleviating several disadvantages associated with fixation by cementation (e.g., premature loosening of the prosthesis, tissue reaction with the bone cement, the need to remove a substantial amount of the patient's bone to provide space for layer of bone cement). Failure of a bone tissue ingrowth fixation, which would of course lead to a premature loosening of the prosthesis, remains as a matter of concern. In a metallic prosthesis comprising a porous coating extending over a non-porous base portion, such failure can occur at the base portion - porous coating interface, at the porous coating - bone interface, within the porous coating, or within the patient's bone outside of the coating.

A variety of different porous metal coatings have been proposed in the prior art for enhancing fixation of a metallic prosthesis by bone tissue ingrowth. Thus, for example, U.S. Pat. No. 3,855,638 discloses a surgical prosthetic device, which may be used as a bone prosthesis, comprising a composite structure consisting of a solid metallic material substrate and a porous coating of the same solid metallic material adhered to and extending over at least a portion of the surface of the substrate. The porous coating consists of a plurality of small discrete particles of metallic material bonded together at their points of contact with each other too define a plurality of connected interstitial pores in the coating. The size and spacing of the particles, which may be distributed in a plurality of monolayers, is such that the average interstitial pore size is not more than about 200 microns, an essential limitation according to the patentee. Additionally, the patentee teaches that the pore size distribution should be substantially uniform from the substrate-coating interface to the surface of the coating. Failure of the bone tissue ingrowth fixation of the prosthesis disclosed in U.S. Pat. No. 3,855,638 tends to occur at the coating-bone interface or in the patient's bone outside of the coating.

Summary of the Invention

It is an object of the present invention to provide a bone prosthesis for fixation by bone tissue ingrowth, which fixation is highly resistant to failure at the substrate-coating and coating-bone interfaces, and within the coating, especially under the cyclic loading conditions experienced by many bone prostheses in use.

This and other objects of the invention are realized with a novel and improved bone prosthesis of the type comprising a substrate of a metallic material and a porous coating of said metallic material bonded to and extending over at least a portion of the surface of the substrate, with said porous coating consisting essentially of a multiplicity of generally ball-shaped particles of said metallic material bonded together at their points of contact, and with said particles defining between themselves a plurality of connected interstitial pores extending through the porous to the surface of the substrate. The improvement of the present invention resides in the detailed nature of the porous coating. Said porous coating comprises first and second layers of said particles, with the particles in the first layer being bonded to the substrate and the first layer being bonded to the second layer. The size and distribution of the particles in each of the layers is such that, as determined by mercury intrusion porosimetry, the average pore size in the porous coating, taken as a whole, is from about 350 microns to about 500 microns and the volume occupied by pores in said coating of less than 250 microns in pore size is no more than about 30 percent of the total volume of porosity in said coating. Because of the large average pore size in the porous coating and the small percentage of porosity volume occupied by small pores, hard tissue grows extensively into the coating, thereby assuring a strong and secure fixation of the prosthesis, while ingrowth of fibrous tissue is minimized. A preferred range for the average pore size in the porous coating is from about 390 microns to about 500 microns. It is also preferred, contrary to the teaching of U.S. Pat. No. 3,855,638, that the porosity and average pore size in the second layer of particles be substantially greater than in the first layer. Although particularly adapted for bone tissue ingrowth fixation, the improved prosthesis of the invention is also highly suited for fixation with bone cement.

In a preferred embodiment of the invention the particles in the first layer are of substantially the same size, i.e. from +30 to −20 U.S. Standard mesh size, as the particles in the second layer.

The present invention further comprises a novel method for affixing a porous coating to at least a portion of the surface of a substrate of a solid metallic material, which process comprises the sequential application and presintering (to establish point bonding) of two layers of ball-shaped particles of said metallic material, followed by a sintering step to promote formation of secure junctions between different particles in the porous coating and between particles in the first applied layer and the substrate.

The present invention comprises additionally a knee joint prosthesis having bearing portions designed so that the function of said prosthesis closely approximates that of the natural knee.

DETAILED DESCRIPTION OF THE INVENTION

The invention will be described in detail with reference to a preferred embodiment thereof, which is a three component knee prosthesis. Reference to this embodiment does not limit the scope of the invention, which is limited only by the scope of the claims. In the drawings:

FIG. 1 is an exploded side view of a right knee joint prosthesis of the invention; and FIG. 2 is an enlarged side view in section of a portion of the prosthesis of FIG. 1 that is adapted to be affixed to the patient's bone by bone tissue ingrowth.

FIGS. 3 and 4 depict an alternate embodiment of the invention.

An improved knee joint prosthesis 1 of the invention is shown in FIG. 1. Prosthesis 1 consists of femoral component 3, tibial component 5 and patellar component 7. The three components are affixed after surgical implantation by bone tissue ingrowth at regions 3a, 5a and 7a, respectively. Thus, for example, after implantation region 5a will lie adjacent to the bone of the resected tibia. An expanded side view in section of a part of region 5a (expanded side views of regions 3a and 7a are identical) is shown in FIG. 2. As shown in FIGS. 1 and 2, tibial component 5 comprises a metallic substrate 20, a plastic tibial bearing surface element 32 and a porous coating 30 bonded to substrate 20 over region 5a. Both substrate 20 and coating 30 are made of the same corrosion resistant surgical implant metal or metal alloy, e.g. titanium or a cobalt-chromium-molybdenum alloy (e.g. Vitallium (Howmedica, Inc.; New York, N.Y.)). Coating 30 consists of a multiplicity of generally spherical particles bonded together at their points of contact. These particles define between themselves a three-dimensional network of interconnected interstitial pores such as the pore shown by the arrow in FIG. 2. In more detail, coating 30 consists of first and second monolayers 22 and 24 of particles. The particles, e.g. particle 16, in layer 22 are bonded to substrate 20, and layer 22 is bonded to layer 24.

As stated earlier, the average pore size in porous coating 30, as determined by the well known technique of mercury intrusion porosimetry, is from about 350 microns to about 500 microns. As used herein, reference to an "average pore size" in a porous structure means that the volume occupied by pores in said structure having less than the "average pore size" is 50 percent of the total volume of porosity in said structure. The volume occupied by pores in coating 30 of less than 250 microns in pore size is, again as determined by mercury intrusion porosimetry, no more than about 30 percent of the total volume of porosity in coating 30. The particles, e.g. 16, in layer 22 are of substantially the same size, i.e. of from +30 to −20 U.S. Standard mesh size, as the particles, e.g. 18, in layer 24. The thickness of coating 30 is from about 1.3 mm. to about 1.5 mm. and the porosity of coating 30 is from about 35 volume percent to about Substrate 20 is a unitary cast Vitallium article which provides both support for the tibial bearing surface element 32 and fixation of the tibial component to the resected tibia. After casting of substrate 20, porous coating 30 may be affixed thereto in the following manner. Region 5a is first cleaned ultrasonically, rinsed and dried. An adhesive binder, e.g. undiluted non-toxic grade photoengraver's glue (Norland Products; New Brunswick, N.J.) is then applied with a firm-bristle artist's brush to region 5a only on substrate 20. Immediately afterward, the first monolayer 22 of spherical particles, e.g. 16, is applied and adhered to the surface of substrate 20 in region 5a at a substantially uniform surface density (particles/mm.²). The spherical particles, e.g. 16, are of from +30 to −20 mesh size. They may be prepared from cast Vitallium or metal alloy bar stock by utilizing a rotating electrode process and then screening the resulting product. The spherical particles are applied to substrate 20, after treatment of the substrate with the adhesive binder, by immersing the substrate into a fluidized bed (10 psi air at inlet) of the dry particles. The substrate is rotated in the bed as required to uniformly coat all of region 5a. The coated substrated is then removed from the bed and dried. The next step in the procedure is to presinter the coated substrate 20, to burn off the binder and to establish point bonding between different particles in layer 22 and between the particles in said layer and the surface of substrate 20, for about 60 minutes at about 1220° C. under vacuum.

The next portion of the procedure is to uniformly coat layer 22 with an adhesive binder and then apply, adhere and presinter the second monolayer 24 of spherical particles, e.g. 18, to the first layer 22. The particles in layer 24 are identical to those in layer 32. The same techniques are utilized as described above in connection with the application, adherence and presintering of layer 22, with one exception, i.e. the binder applied to layer 22 is diluted, e.g. five parts non-toxic photoengraver's glue diluted with one part distilled water, to reduce its viscosity. As a result, layer 22 is substantially uniformly coated with the particles of layer 24.

The next step in the procedure is to sinter the coated substrate, e.g. in a furnace for about 30 minutes at about 1300° C. and 100 microns Hg pressure under an argon atmosphere, in order to cause the formation of strong and secure junctions, e.g. necks 26 and 28, between different particles in coating 30 and between the particles in layer 22 and substrate 20. Subsequently, the coated substrate should be heat treated to eliminate internal stresses, cooled, cleaned, passivated and sterilized. As an inherent result of this coating procedure, the particle surface density (particles/mm.²) in layer 24 is substantially less than in layer 22 and, therefore, the porosity and average pore size in layer 24 are substantially greater than in layer 22.

The improved prosthesis of the present invention can exist in a wide variety of embodiments, e.g., knee joint components, hip joint components, bone plates, bone bridges, bone staples, intramedullary nails, dental implants.

Of critical importance to the success of the present invention is the pore size distribution in the porous coating. Because the average pore size in the coating is at least about 350 microns and the volume occupied by pores in the coating of less than 250 microns in pore size is no more than about 30 percent of the total volume of porosity in the coating, hard bone tissue grows extensively into the coating and fibrous tissue ingrowth is minimized. Additionally, the porous coating itself and its junction with the substrate are very strong and resistant to failure under loading. As a result, the bone tissue ingrowth fixation of a prosthesis of the present invention is highly resistant to failure; ultimately, failure of the fixation forced by the application of exceedingly high levels of stress will tend to result from fracture of the patient's bone itself outside of the coating.

When the manufacturing procedure described in detail above is carried out to coat a cast Vitallium substrate with two layers of spherical Vitallium particles of from +30 to −20 U.S. Standard mesh size, a very strong composite article with the following range of pore size distributions, as determined by mercury intrusion porosimetry, is obtained:

| Pore Size (Diameter) in Microns | Cumulative Percentage of Total Volume of Porosity in Coating Occupied by Pores Smaller than Indicated Pore Size |
|---|---|
| 100 | 5 to 9 |
| 150 | 8 to 14 |
| 200 | 12 to 20 |
| 250 | 18 to 27 |
| 300 | 24 to 35 |
| 350 | 32 to 44 |
| 400 | 40 to 52 |

| Pore Size (Diameter) in Microns | Cumulative Percentage of Total Volume of Porosity in Coating Occupied by Pores Smaller than Indicated Pore Size |
| --- | --- |
| 390 to 465 | 50 |
| 450 | 47 to 59 |
| 500 | 55 to 67 |
| 550 | 62 to 73 |
| 600 | 68 to 78 |
| 650 | 74 to 83 |
| 700 | 79 to 86 |
| 750 | 83 to 89 |
| 800 | 86 to 92 |
| 850 | 89 to 93 |
| 900 | 91 to 95 |
| 950 | 93 to 96 |
| 1000 | 94 to 97. |

These composite Vitallium articles, which are preferred embodiments of the present invention, exhibit extraordinary strength in tension (tensile strength greater than 7000 psi) and shear (shear strength greater than 7000 psi) and under cyclic loading to determine fatique strength (no failure after $4 \times 10^6$ cycles at 3000 psi).

The surgical implantation of an improved prosthesis of the present invention is a straightforward procedure. The prosthesis will generally be provided with a porous coating wherever it is to come into contact with the prepared (e.g. resected) bone of the patient. In certain instances, e.g. the implantation of femoral component 3 in FIG. 1, initial stabilization for tissue ingrowth is achieved by press-fitting the prosthsis in place. In other instance, e.g. the implantation of tibial component 5, initial stabilization is achieved with an expanding fixation screw 34. Bone tissue ingrowth commences immediately after implantation. Substantial fixation by bone tissue ingrowth will occur within about six weeks after implantation. Bone preparation and implantation of the knee prosthesis 1 shown in FIG. 1 is preferably accomplished with the use of the instrumentation and techniques described in my concurrently filed co-pending United States Patent Application Ser. No. 350,013, filed Feb. 18, 1982, entitled "Prosthetic Knee Implantation", now U.S. Pat. No. 4,646,729. The collateral ligaments will ususlly. be preserved when the prosthesis 1 is implanted.

In FIG. 1, porous coated lateral fixation posts 56, 58 and 60 are shown on the three components. Indentical medial fixation posts are hidden in the figure.

A further aspect of the invention resides in the relative configurations of the bearing portions of femoral and tibial components 3 and 5 of knee prosthesis 1 (see FIG. 1), which is a prosthesis for the right knee. Femoral component 3 comprises two condylar bearing poritons (only the lateral bearing portion 50 is shown in FIG. 1). The lateral and medical femoral bearing portions are substantially identical. The curvature of the bearing surface of bearing portion 50 increases from the anterior region 52 in contact with the tribial componoent at extension of the joint to the posterior region 54 in contact with the tibial component at full flexion. The curvature of the bearing surface in region 52 is substantially identical to that of the corresponding region of the natural fermoral bearing surface, while the curvature of the bearing surface in region 54 is substaiilly greater than that of the corresponding region of the natural fermoral bearing surface. The femoral bearing surfaces are substantially horizontal in the coronal plane.

The tibial bearing surface element 32 comprises two condylar bearing portions (only the lateral bearing portion is shown in FIG. 1). The bearing surface of the lateral tibial bearing portion is curved in anterior region 62, flat in central region 64 (which is sloped slightly downwardly and posteriorly) and again curved in posterior region 66. The curvature in region 66 is greater than the curvature in region 62. The bearing surface of the medial tibial bearing portion is similar to that of the lateral tibial portion, but has a shorter flat section in its central region. The tibial bearing surfaces are substantially horizontal in coronal planes.

As a result of the configurations discussed above of the femoral and tibial bearing surfaces, the natural anatomical joint space differential and collateral ligamentous balance are preserved during the flexion of the prosthetic knee joint 1. Torque rotation curves obtained with said prosthetic knee joint are similar to those obtained with the natural knee. Prosthesis 1 thus closely reproduces the motion of the natural knee and experiences reduced torsional and shear stress at fixation interfaces.

FIGS. 3 and 4 are top and side plan views, respectively, of an alternate right tibial substrate having a conventional tibial peg 70 adapted to be inserted into a prepared hole in the resected tibia. A porous coating for bone tissue ingrowth is provided at the regions to be adjacent the resected tibia, including the region of the surface of tibial peg 70. On the rare instances when it might be desired to remove the tibial component from the body, this task is facilitated by the provision of slots 72, 74 and 76 in the metal or metal alloy portion of the component (see FIG. 3). The surgeon can readily cut away all of the component other than peg 70 by cutting along the slots and then horizontally under the bearing portion regions. He can then readily cut around and remove the peg without excessive destruction of the patient's natural bone.

We claim:

1. A method for affixing a porous coating to at least a portion of the surface of a bone prosthesis substrate made of a solid metallic material, with said porous coating consisting essentially of a multiplicity of ball-shaped particles of said metallic material bonded together at their points of contact, comprising the steps of
   (a) applying a binder to at least a portion of the surface of said substrate;
   (b) applying a first layer of said particles to the surface of said substrate at a substantially uniform surface density, said first layer being adhered thereto by said binder;
   (c) heating the coated substrate resulting from step (b) under vacuum for a time and at a temperature sufficient to establish point bonding between different particles in said first layer and between the particles in said first layer and the surface of said substrate;
   (d) applying a binder to the surface of said first layer;
   (e) applying a second layer of said particles to the surface of said first layer at a substantially uniform surface density, said second layer being adhered thereto by said binder;
   (f) heating the coated substrate resulting from step (e) under vacuum for a time and at a temperature sufficient to established point bonding between particles in said first layer and particles in said second layer; and (g) sintering the coated substrate resulting from step (f) under vacuum for a time and at a temperature sufficient to promote formation of secure junctions between different particles in said porous coating and between particles in said first layer and said substrate, with the particles in said first layer being of substantially the same size as the particles in said second layer, and with the particles in said first and second layers being of from +30 to −20 mesh size.

2. A method of claim 1 wherein the particle surface density in said first layer is substantially greater than in said second layer, whereby the porosity and average pore size in said second layer are substantially greater than in said first layer.

* * * * *